United States Patent [19]
Smith

[11] Patent Number: 5,145,333
[45] Date of Patent: Sep. 8, 1992

[54] FLUID MOTOR DRIVEN BLOOD PUMP

[75] Inventor: William A. Smith, Lyndhurst, Ohio

[73] Assignee: The Cleveland Clinic Foundation, Cleveland, Ohio

[21] Appl. No.: 486,953

[22] Filed: Mar. 1, 1990

[51] Int. Cl.⁵ .............................................. F04D 7/00
[52] U.S. Cl. .................................... 417/405; 415/202;
415/900; 416/223 R; 417/407; 600/16; 623/3
[58] Field of Search ......................... 415/900, 202, 203;
417/405, 407; 600/16; 623/3; 416/197 R, 223 R

[56] References Cited

U.S. PATENT DOCUMENTS

| Re. 26,306 | 11/1967 | Jekat et al. | |
| 932,240 | 8/1909 | Beale et al. | 417/405 |
| 2,700,935 | 1/1955 | Teague, Jr. | |
| 3,608,088 | 9/1971 | Dorman et al. | 623/3 |
| 4,135,253 | 1/1979 | Reich et al. | |
| 4,173,796 | 11/1979 | Jarvik | |
| 4,296,500 | 10/1981 | Monties et al. | |
| 4,594,060 | 6/1986 | Schwab | |
| 4,625,712 | 12/1986 | Wampler | |
| 4,704,121 | 11/1987 | Moise | |
| 4,927,407 | 5/1990 | Dorman | |

Primary Examiner—Gerald A. Michalsky
Attorney, Agent, or Firm—Fay, Sharpe, Beall, Fagan, Minnich & McKee

[57] ABSTRACT

A rotary blood pump includes an impeller in a pump chamber driven by a fluid motor. In a first preferred embodiment, the fluid motor includes a rotary member having a series of cupped fluid reactive surfaces that receive a tangential inlet pressurized fluid flow. The cupped surfaces direct the fluid to opposite sides of the rotary member. Passages extending through the rotary member convey fluid from one side of the rotary member to the other. In a second preferred arrangement, the fluid motor is defined by a positive displacement motor. In a third embodiment, the fluid motor is separated from the pump chamber by a wall. Both biocompatible and non-biocompatible fluids can be used to drive the fluid motor.

11 Claims, 6 Drawing Sheets

FLUID MOTOR DRIVEN BLOOD PUMP

BACKGROUND OF THE INVENTION

This invention pertains to the art of blood pumps, and more particularly to rotary blood pumps. The invention is applicable to a fluid motor driven pump that may be implanted in a body cavity and will be described with particular reference thereto. However, it will be appreciated that the invention has broader applications and may be employed in related environments and applications.

Available rotary blood pumps, although varying in different aspects of their design, typically have one common feature. Specifically, most known rotary blood pumps employ an electric motor as the prime mover for the device. Although deemed to be reliable from an operational standpoint, electric motors are undesirable for other reasons. For example, the size of an electric motor is a primary drawback. When faced with scaling down or miniaturizing components due to the limited space available in the body cavity, it is believed that other smaller drive arrangements would be equally suitable.

Yet another deficiency associated with electric motors is the need to bring electricity into the body. Although precautions are taken and believed to adapt electric motors to internal use, these safeguards can be eliminated if the reason for the safeguards is itself eliminated; namely, the electric motor.

Due to the nature of electric motors, heat is produced during operation of the motor and it becomes necessary to cool the motor. Typically, fluid is continuously circulated around the motor and the heat transferred thereto resulting in a net cooling of the blood pump. Many of these rotary blood pumps thus supply sealing or cooling fluid to the pump assembly for just such a purpose.

As a result of the conventional use of electric motors and the associated need to cool the motor, plural supply lines must also enter the body cavity. This results in a complex array of lines that each control different operational aspects of the pump. Thus the need to reduce the number of skin penetrations becomes another consideration when evaluating the continued use of an electric motor as the prime mover for a blood pump.

It has been deemed desirable to maintain all of the above benefits of a rotary blood pump having an electric motor and overcome various deficiencies in the prior arrangements.

SUMMARY OF THE INVENTION

The present invention contemplates a new and improved rotary blood pump that provides all of the above advantages and provides a simple, efficient fluid drive arrangement.

According to the present invention, the rotary blood pump includes a housing having a pump chamber defined therein. An impeller is received in the chamber for rotation about an axis and pressurizes fluid received through an inlet to an outlet. The fluid motor means is associated with the impeller for imparting rotary movement thereto.

According to another aspect of the invention, a first fluid line communicates with the fluid motor means to convey pressurized fluid thereto. A second fluid line carries fluid from the fluid motor means.

According to a still further aspect of the invention, the fluid inlet conveys pressurized fluid to a rotary member, preferably impinging thereon in a tangential arrangement.

According to still another aspect of the invention, the second fluid line outlets fluid in a generally axial direction from the housing.

According to still another aspect of the invention, a passage is provided through the rotary member to permit fluid to pass axially from one side of the rotor member to the other.

According to an alternate arrangement, a purge seal is provided so that non-biocompatible drive fluids can be utilized.

According to yet another alternate arrangement, the fluid motor is isolated from the bearing cavity so that again, a non-biocompatible drive fluid can be utilized with a simplified unpurged seal arrangement.

A principal advantage of the invention is the reduced complexity of the rotary blood pump.

Another advantage of the invention resides in the combined benefits of a fluid drive motor such as cooling, biocompatibility, and reduced size.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, preferred and alternate embodiments of which will be described in detail in the specification and illustrated in the accompanying drawings which form a part hereof, and wherein.

DETAILED DESCRIPTION OF THE PREFERRED AND ALTERNATE EMBODIMENTS

Figure 1:
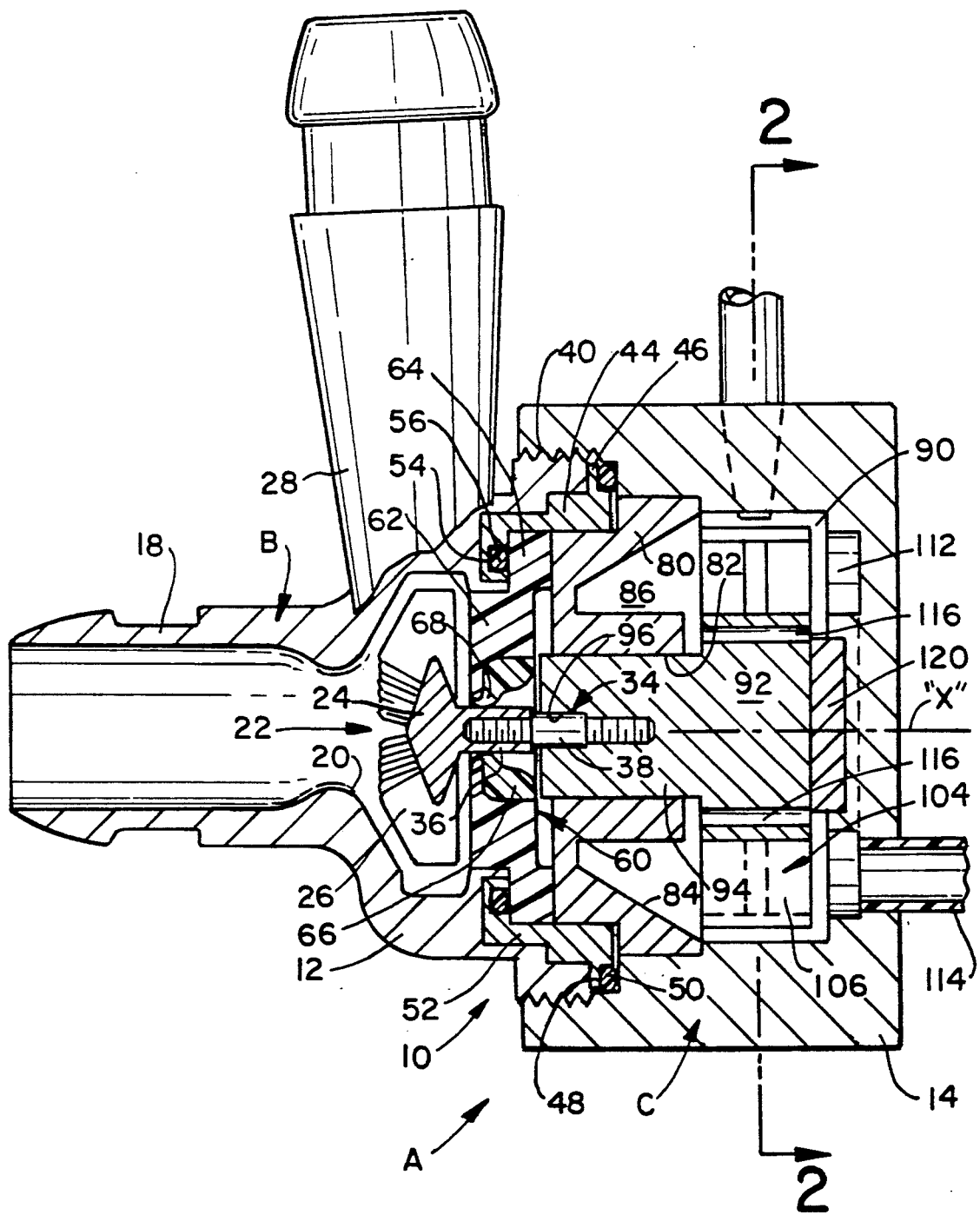
FIG. 1 is a longitudinal cross-sectional view of a first preferred embodiment of the invention.

Referring now to the drawings wherein the showings are for purposes of illustrating the preferred and alternate embodiments only, and not for purposes of limiting same, the FIGURES show a rotary blood pump A having a pumping section B and a motor section C. The blood pump is sized for implanting if desired, or can alternately be used as an external assist device.

Figure 2:
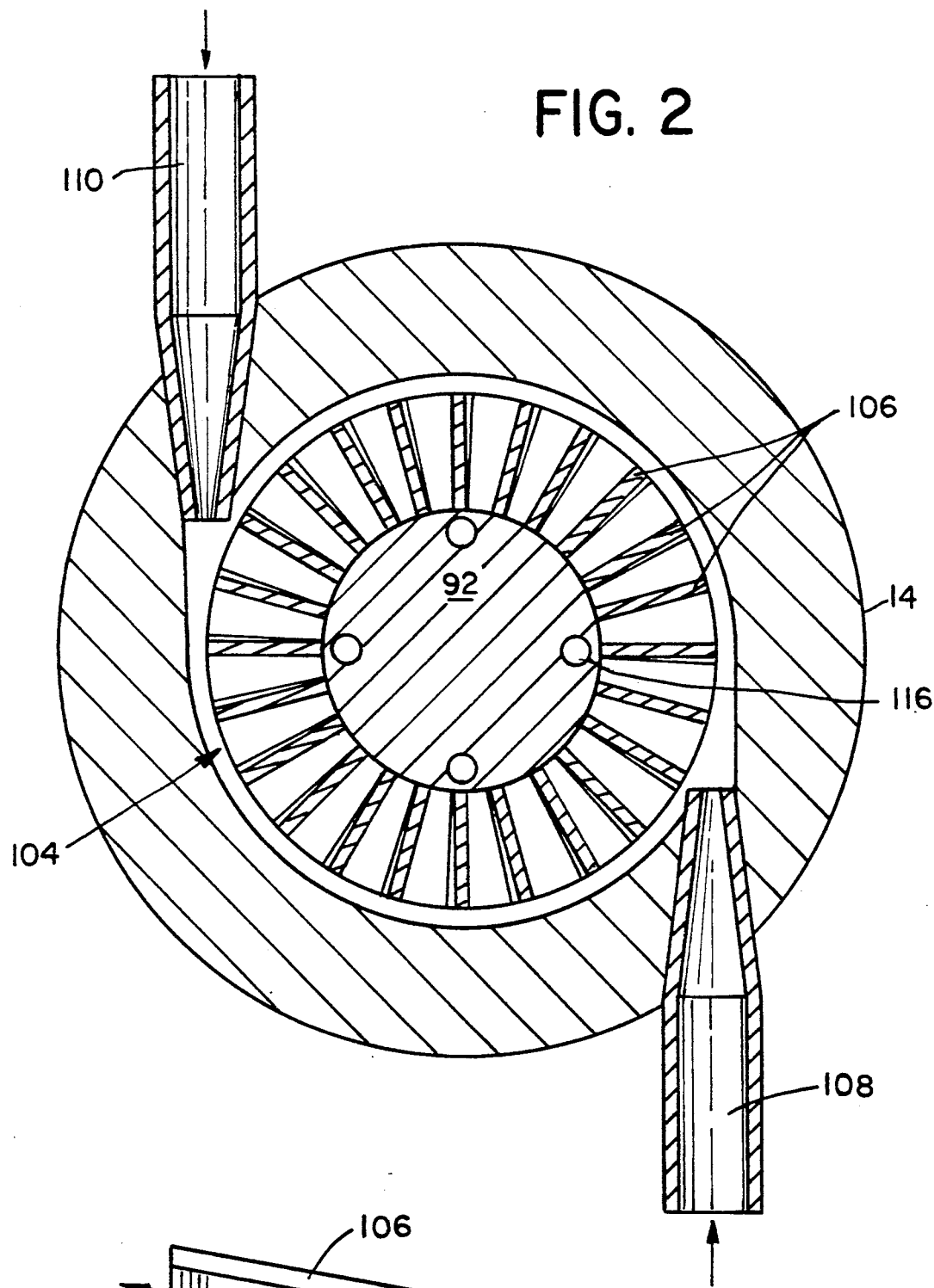
FIG. 2 is a cross-sectional view taken generally along the lines 2—2 of FIG. 1.
Figure 3:
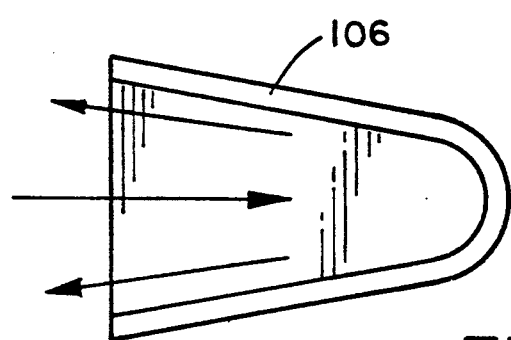
FIG. 3 is a plan view of a preferred fluid reactive surface of the drive motor.

More particularly, and with reference to FIGS. 1-3, the blood pump includes a housing 10 having a first portion 12, generally defining the pumping section of the pump, secured to a second portion 14, generally defining the motor section of the pump. An axial inlet 18 introduces blood to a pump chamber 20 defined in the housing first portion. Energy is imparted to the blood by an impeller 22 adapted for selective rotation in the pump chamber. The impeller includes a central hub 24 and plural vanes or blades 26 extending axially and radially outward from the hub. A radial or tangential outlet 28 also communicates with the pump chamber and is adapted to receive the energized blood flow as it exits from the periphery of the impeller.

Extending axially rearwardly from the hub is a drive shaft 34 having a first portion 36 integrally formed with the impeller hub. The shaft first portion is joined or secured to a second portion 38. As illustrated, the first and second portions of the drive shaft are threadedly interconnected, although other connecting arrangements may be utilized without departing from the scope and intent of the subject invention.

The first and second portions 12, 14 of the housing are preferably sealingly secured together. According to the illustrated arrangement, the first portion is threadedly received in the housing second portion as denoted by reference numeral 40. The sealing arrangement is effected by a circumferentially continuous ring 44 having an outer shoulder 46 axially interposed between the housing first and second portions. The shoulder includes a first groove 48 disposed along a radial outer portion in facing relation with the housing second portion 14. The first groove is adapted to receive a sealing member such as first 0-ring 50. A radially inward extending shoulder 52 likewise includes a second groove 54 adapted to receive a seal member such as second 0-ring 56. This second 0-ring provides a sealing interface between the housing and a generally conventional contact-type seal assembly 60.

The seal assembly 60 includes a seal baffle or support ring 62 having an outer radial portion 64 radially captured by ring 44 and in sealing engagement with 0-ring 56. A soft sealing member 66 is, in turn, supported along a radially inner portion of the support ring. Preferably, the soft sealing member includes a circumferentially continuous edge or lip 68 that sealingly engages the periphery of the drive shaft, particularly the drive shaft first portion 36 in this embodiment. Thus, blood in the pump chamber 12 is prevented from entering the housing second portion 14.

An enlarged bearing 80 extends axially rearwardly from the ring 44 and the support ring 62. The bearing has an annular conformation, operatively engaging the housing second portion along its outer circumference and defining a bore 82 along its inner circumference that maintains a slight radial gap with the drive shaft. Further, the bearing is irregularly shaped along a rear face. Particularly, a cut out region 84 defines a cavity or reservoir 86, the function of which will become more apparent hereinbelow.

Within the housing second portion 14, a chamber 90 receives a rotodynamic fluid motor defined by rotary member 92. A stem 94 extends axially from the rotary member and is closely received in the bore 82 of the bearing. The stem also includes a recess 96 at one end that receives the drive shaft second portion 38 therein. Again, a threaded interconnection between the drive shaft second portion and the stem is illustrated, although other connections may be utilized without departing from the scope and intent of the subject invention. A radially enlarged portion of the rotary member 92 defines a fluid reactive surface 104. According to the preferred arrangement, the fluid reactive surface includes a series of cupped blades 106 (FIG. 3). Any desirable number of blades may be disposed along the circumference of the fluid reactive surface and all the blades are oriented in substantially the same manner to permit rotational movement of the rotary member about axis "x".

With particular reference to FIG. 2, the orientation of first or inlet fluid lines 108, 110 is best shown. Preferably, these fluid lines provide pressurized fluid from an associated source (not shown) and intersect the motor chamber tangentially. The pressurized fluid is thus directed toward the periphery of the rotary member, contacting the cupped blades 106. The cupped blades, due to their configuration, divide the flow to axially opposite sides of the rotary member as schematically illustrated by the arrows in FIG. 3. Ideally, half of the pressurized fluid is directed toward the cavity 86 in the bearing. The remaining half of the working fluid is received axially rearwardly of the rotary member in an annular collector groove 112 and exits the housing 10 through outlet 114.

The portion of the pressurized fluid that is directed toward bearing cavity 86 also eventually exits the housing through outlet 114. As best shown in FIG. 1, axially extending openings or passages 116 are defined in the rotary member radially inward from the fluid reactive surfaces. The openings permit the working fluid to escape from bearing cavity 86 to the rear face of the rotary member and eventually to outlet 114. A pressure drop is encountered through the opening so that the rotary member is urged toward the outlet. The chamber includes a thrust plate 120 adapted to accommodate for the slight axial pressure imbalance on the rotary member. In this manner, undue axial forces are not imposed on the bearing member, seal assembly, etc.

Figure 4:
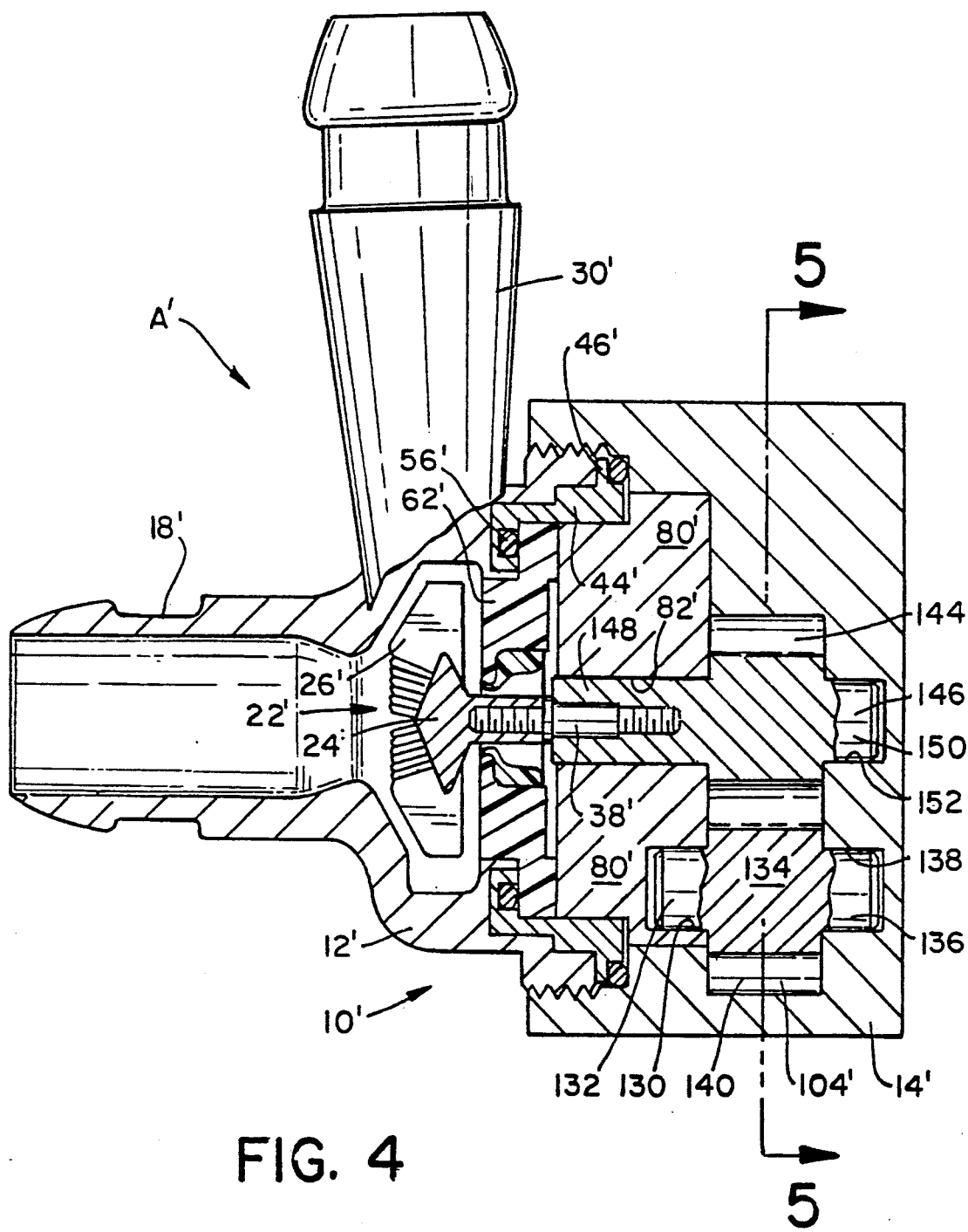
FIG. 4 is a longitudinal, cross-sectional view of an alternate embodiment according to the subject invention.
Figure 5:
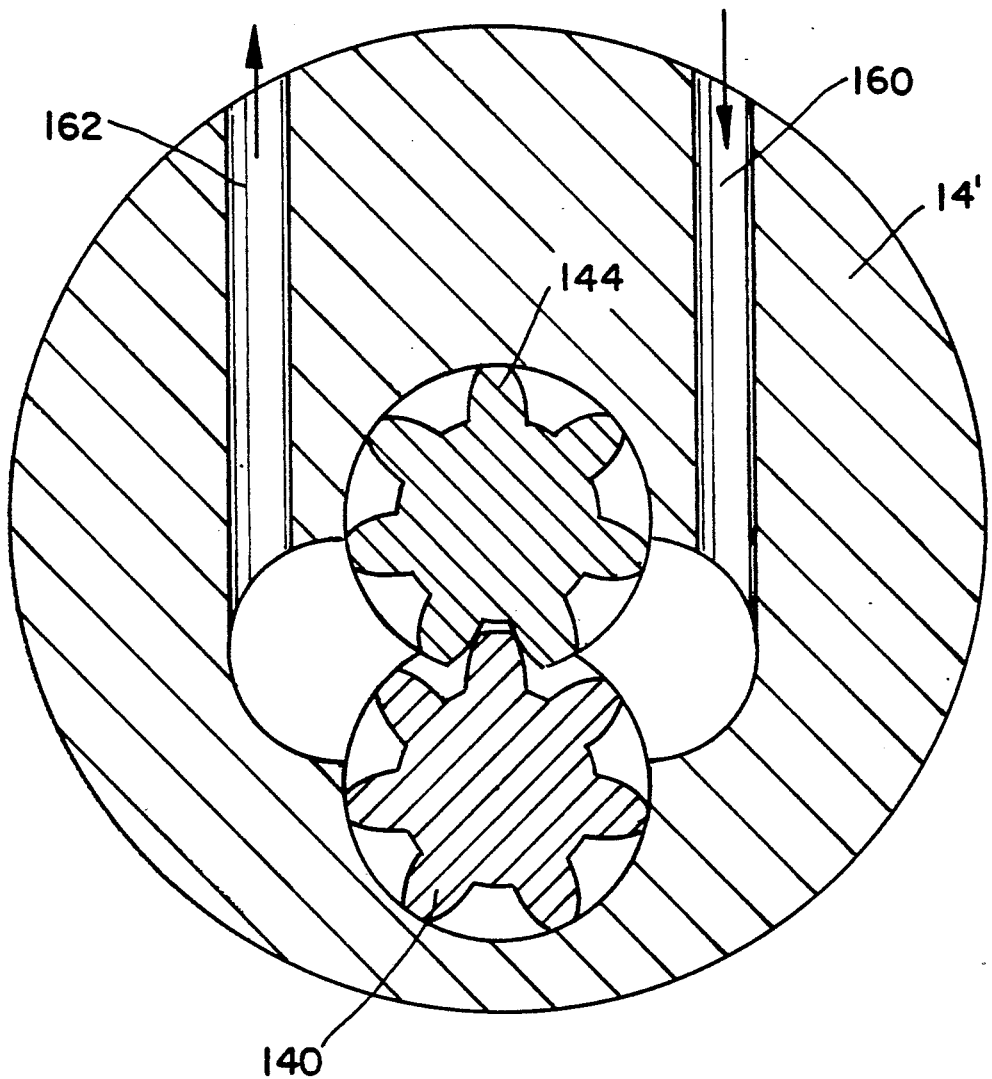
FIG. 5 is a cross-sectional view taken generally along the lines 5—5 of FIG. 4.

An alternate embodiment shown in FIGS. 4 and 5 incorporates a positive displacement fluid motor to drive the blood pump. For ease of description and illustration, like numerals with a primed (') suffix will refer to like elements, while new numerals will refer to new elements.

In this illustration, seal baffle 62' is shown as a non-contacting purged arrangement. Bearing 80' is somewhat modified so that bore 82' is reduced in diameter. The cut out region in the FIG. 1 embodiment is also eliminated in this arrangement, although a new recess 130 is defined in a rear face of the bearing. The recess receives one end 132 of an integrally formed shaft of a first rotary member 134. The opposite end 136 of the shaft is rotatably received in a similar recess 138 formed in the housing second portion 14'. The first rotary member includes a series of gear teeth 140 defined about the periphery. The gear teeth in this gear motor arrangement serve the dual function of being fluid reactive surfaces 104' as well as functioning as sealing surfaces between the high and low pressure sides of the motor.

The second rotary member also includes an integrally formed shaft having a first, elongated end 148. The shaft first end is adapted to threadedly receive drive shaft second portion 38'. An opposite end 150 of the shaft is received in a second recess 152 formed in the rear wall of the housing. Thus, the second rotary member is adapted for rotation about an axis generally parallel to the rotational axis of the first rotary member and colinear with the rotational axis of the impeller A series of peripheral teeth 144 engage the teeth 140 of the first rotary member to advantageously transfer power from the first member to the second member. In the preferred arrangement, a like number of teeth are disposed on each of the rotary members to provide a 1:1 ratio, although other gear ratios can be utilized without departing from the subject invention.

According to this gear motor arrangement, pressurized fluid provided through a first or inlet fluid line 160 contacts the teeth of the rotary members (FIG. 5). The fluid imparts rotary motion to the second member and impeller, and in addition the force generated by the pressure difference across the first member is transmitted through the gear mesh to the impeller. Thereafter, the pressurized fluid leaves the housing through a second or outlet fluid line 162.

The embodiments described above are designed so that the drive fluid is biocompatible with a patient's body, particularly the blood. Limited mixing of the driving fluid and the patient's blood may occur so that only selected fluids can be used in those situations. It is critical to design and monitor the fluid loading on a patient that will be associated with those blood pump arrangements.

Figure 6:
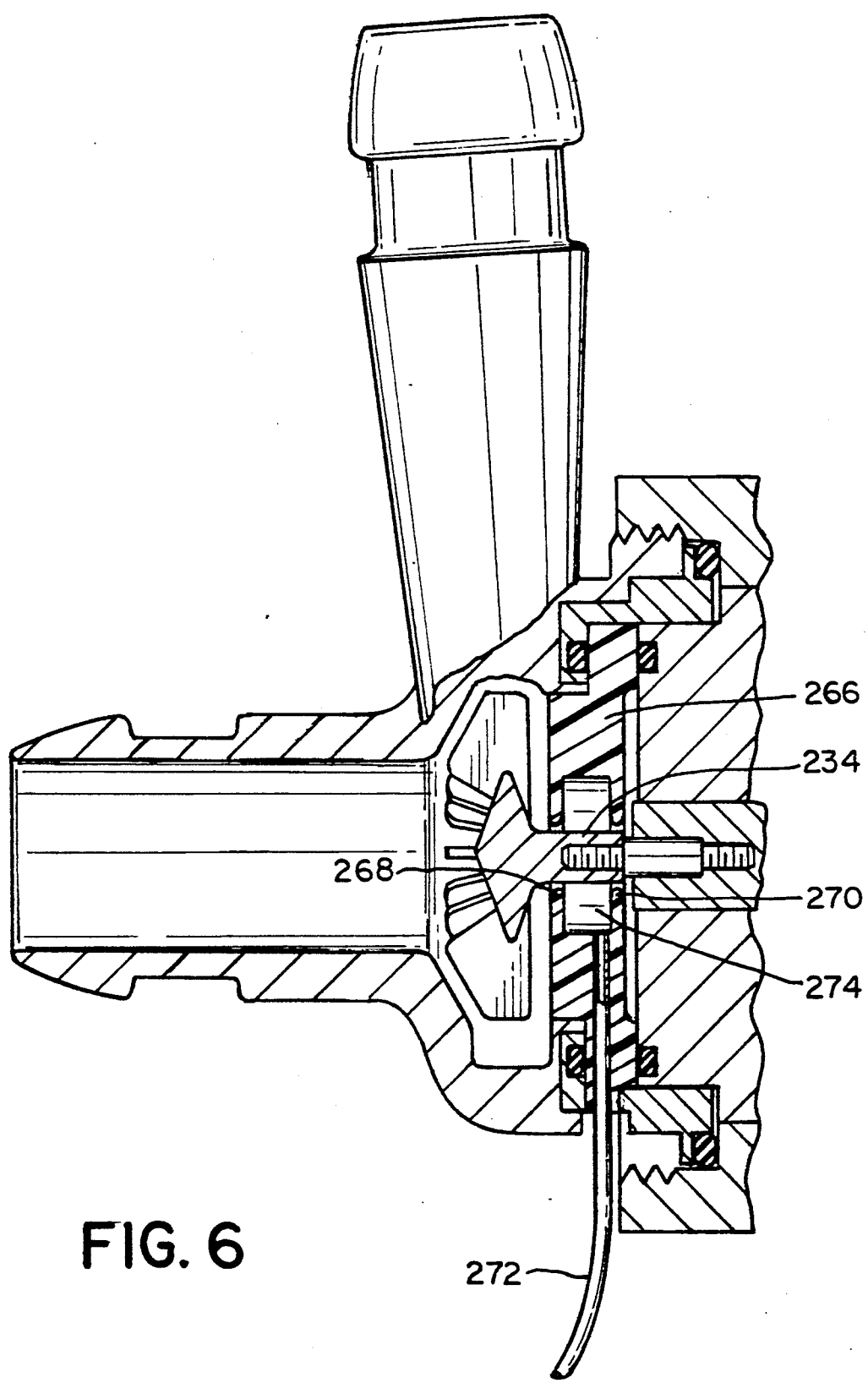
FIG. 6 is longitudinal, partial cross-sectional view of a seal arrangement applicable to selected versions of a fluid motor driven blood pump.

FIG. 6 is a purge seal version of a fluid motor driven pump particularly adapted to the use of non-biocompatible drive fluids. That is, the fluid used to drive the pump is not compatible like the fluids anticipated for the embodiments of FIGS. 1-5. For example, compressed air and tap water are just two types of non-biocompatible fluids that are envisioned for alternate use as the drive fluid in the following embodiments.

As shown in FIG. 6, near-contact of the support ring 266 is provided at two axially spaced regions 268, 270 of the drive shaft 234. The near-contact regions define purge seals in which the first purge seal 268 faces the pump chamber, or blood side of the pump, while the second purge seal 270 faces the fluid motor, or drive fluid side of the pump. A biocompatible purge fluid is supplied through a passage 272 to an annular cavity 274 disposed between the near-contact regions. The purge fluid is provided at a pressure greater than the blood or drive fluid pressure. This seal arrangement assures that blood/drive fluid intermixing does not occur.

Figure 7:
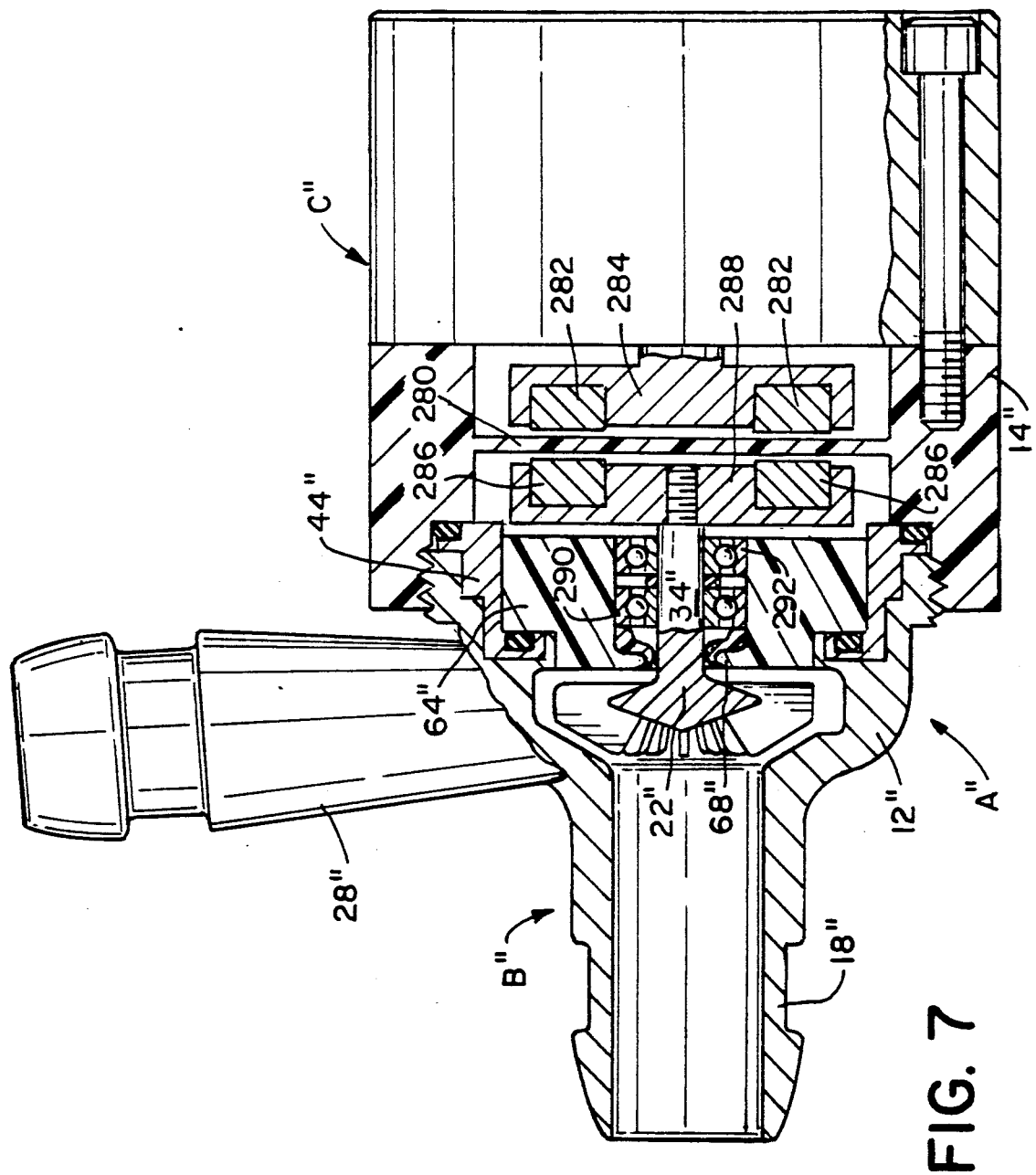
FIG. 7 is a longitudinal, partial cross-sectional view of an alternate embodiment of a fluid driven blood pump isolating the fluid for driving the motor from the blood.

In FIG. 7, the drive motor is still fluid driven but an unpurged seal arrangement is used. Again, for ease of illustration and description, like parts will be identified by like numerals with a double primed (") suffix and new elements will be identified by new numerals. More particularly, the fluid drive motor is isolated from the bearing cavity by a solid wall 280. Preferably the wall is constructed from a magnetically inert material. In this manner, drive magnets 282 provided on fluid driven rotary member 284 can operatively drive the driven magnets 286 on the driven member 288. The driven member is, in turn, secured to the drive shaft 34" so that rotational motion is effectively transferred to the impeller 22". By magnetically coupling the impeller to the drive motor, a simplified unpurged seal can be used. Specifically, the FIG. 7 embodiment employs a suitable contact seal arrangement 68" to exclude blood from the bearing cavity.

Since the drive shaft is not physically connected to the fluid motor it becomes necessary to support the impeller and drive shaft in the blood pump. Accordingly, support bearings 290, 292 are axially spaced along the drive shaft to facilitate ease of rotation of the impeller.

The invention has been described with reference to the preferred and alternate embodiments. Obviously modifications and alterations will occur to others upon a reading and understanding of this specification. For example, modified fluid motors such as other rotodynamic motors i.e., impulse or reaction turbines, etc., or positive displacement fluid driven motors such as piston or vane motors can be effectively used in accordance with the principles and structural arrangements described above. It is intended to include all such modifications and alterations in so far as they come within the scope of the appended claims or the equivalents thereof.

Having thus described the invention, it is now claimed:

1. A rotary blood pump comprising:
   a housing having an inlet and outlet in fluid communication with a pump chamber;
   an impeller operatively received in said chamber for rotation about a first axis, said impeller conveying blood from said inlet to said outlet;
   a fluid motor means operatively associated with the impeller for imparting rotary movement thereto about the first axis;
   a first fluid line adapted to convey pressurized fluid from an associated source to said fluid motor means;
   a second fluid line adapted to convey fluid from said fluid motor means;
   said fluid motor means including a rotary member having a plurality of cupped surfaces disposed along the periphery thereof and disposed adjacent said first fluid line for rotation in response to the pressurized fluid from the associated source, said cupped surfaces directing pressurized fluid toward axially opposite sides of the rotary member; and
   means for conveying fluid flow in directions generally parallel to the first axis from one side of the rotary member to the other, said conveying means being defined by passages extending through said rotary member.

2. The blood pump as defined in claim 1 further comprising a magnetic coupling assembly transferring rotary motion from the fluid motor means to the impeller.

3. The blood pump as defined in claim 2 further comprising a wall member disposed between the fluid motor means and the pump chamber.

4. The blood pump as defined in claim 1 wherein said first fluid line tangentially intersects said housing.

5. The blood pump as defined in claim 1 wherein said second line axially intersects said housing.

6. The blood pump as defined in claim 1 further comprising a thrust surface disposed on the same side of the rotary member as the intersection of said second fluid line with said housing.

7. The blood pump as defined in claim 1 further comprising a seal means interposed between the pump chamber and fluid motor means.

8. The blood pump as defined in claim 7 wherein the seal means is defined by a purge seal.

9. The blood pump as defined in claim 8 wherein the purge seal uses a biocompatible fluid distinct from the fluid used to drive the fluid motor means.

10. The blood pump as defined in claim 8 wherein the purge seal uses the same fluid as used to drive the fluid motor means.

11. The blood pump as defined in claim 7 wherein the seal means is defined by a contact seal.

* * * * *